United States Patent
Levy et al.

(10) Patent No.: US 6,592,860 B1
(45) Date of Patent: Jul. 15, 2003

(54) COMPOSITION AND APPLICATOR FOR TOPICAL SUBSTANCE DELIVERY

(75) Inventors: Guy Glickson Levy, Newport News, VA (US); Carl Anthony Williams, Radford, VA (US); James David Rancourt, Blacksburg, VA (US); Christine June Gerdon, Blacksburg, VA (US)

(73) Assignee: Soluble Systems, LLC, Newport News, VA (US)

( * ) Notice: Subject to any disclaimer, the term of this patent is extended or adjusted under 35 U.S.C. 154(b) by 0 days.

(21) Appl. No.: 09/580,679

(22) Filed: May 30, 2000

(51) Int. Cl.[7] .......................... A61K 31/74; A61K 9/14; A61F 13/00
(52) U.S. Cl. .................... 424/78.08; 424/422; 424/484; 424/434
(58) Field of Search ............................... 424/422, 78.08, 424/484, 434; 525/116

(56) References Cited

U.S. PATENT DOCUMENTS

| | | | |
|---|---|---|---|
| 4,351,922 A | * 9/1982 | Yoshida et al. | 525/116 |
| 4,680,336 A | 7/1987 | Larsen et al. | |
| 4,900,552 A | * 2/1990 | Sanvordeker et al. | 424/422 |
| 5,614,223 A | 3/1997 | Sipos | |
| 5,684,058 A | 11/1997 | Nunez et al. | |
| 5,968,500 A | * 10/1999 | Robinson | 424/78.08 |
| 6,103,266 A | * 8/2000 | Tapolsky et al. | 424/484 |

* cited by examiner

*Primary Examiner*—Jose' G. Dees
*Assistant Examiner*—R DeWitty
(74) *Attorney, Agent, or Firm*—Peter E. Rosden

(57) ABSTRACT

A polymerized hydrogel composition and applicator for hydrating or dehydrating a surface, particularly a dermatological surface, to which it is applied and a method for forming the composition. The composition is comprised of a mixture of two polymerizable materials, a two-part redox catalyst system and a two-part polymerization medium. The percentage by weight of each element in the composition may be varied within stated percentage ranges. The rate at which hydration or dehydration occurs may be controllably altered by varying the percentages of certain of the composition elements. The applicator includes a thermoplastic center section and two reservoir sections each having a reservoir storage area for holding moisture and/or medicaments. The composition is mechanically bonded onto each of the reservoir sections and then hydrated. The applicator is designed for insertion into a human mouth after hydration and is used for treating xerostomia.

28 Claims, 3 Drawing Sheets

COMPOSITION AND APPLICATOR FOR TOPICAL SUBSTANCE DELIVERY

TECHNICAL FIELD

The subject invention relates generally to the delivery of moisture to a dermatological surface, and, more particularly, to a composition for providing soluble medicaments and moisture to such surfaces when used either alone or in conjunction with a device.

BACKGROUND OF THE INVENTION

The ability to provide a controlled, variable release of soluble medicaments or aqueous substances in a topical manner is desirable for treating a variety of diseases and ailments. For example, the general aging of the population is accompanied by a concomitant increase in the number of cases of dry mouth, also referred to as xerostomia. This is a condition in which salivary flow is either decreased or undergoes a compositional change. Not only is this affliction irritating, it can also aggravate problems involving swallowing and speaking and may even lead to increased tooth decay. In the elderly xerostomia is particular dangerous since it may interfere with eating and result in malnutrition.

Such a salivary alteration can occur as a natural glandular disfunction, as the result of any of a number of illnesses including rheumatoid arthritis, Lupus, diabetes, HIV and Sjögrens syndrome, as a side effect of radiation or chemotherapy treatments for other illnesses, through ingestion of over-the-counter and prescription drugs or may even arise out of psychological conditions such as stress and depression. Since dry mouth may be either a temporary or a permanent condition, the importance of finding an inexpensive, simple method for providing relief from its symptoms is especially great.

The prior art has focused on either osmolar exchange of medicaments or on the imbibement of a saliva substitute or water for the dissolution of subsequently delivered medications. Research into this area has focused mainly on developing improved durability of compositions inserted directly into the mouth. An integrated approach for providing medication or water in the mouth through a controlled release delivery system incorporating a gel and/or polymer into a mechanical device has been underemphasized in the art.

Numerous issues must be addressed in developing such an integrated delivery system. First, the delivery system must be biocompatible since it is designed for use in the oral cavity. Second, the system must be pleasant and easy to use as it will be distributed to the general public. It should not be accompanied by any chemical or repellent taste or smell. Third, it must achieve a comfortable fit inside the user's mouth. This point is particularly important since, due to dryness, the mouth may be prone to infection and is likely to be highly sensitive. A fourth consideration is safety. The system must exhibit resistance to microbial growth and, since it will be in use primarily at night, must not present a choking or swallowing risk to the user while asleep. Finally, such a system would have to exhibit physical stability and durability along with the capability to release a known amount of fluid into a patient's mouth at a controlled, but variable, rate for a prolonged and predictable period of time.

It is known to have syringe applicators or encapsulated sponges for delivering medicaments or moisture. However, compositions used for the purpose of topical delivery of medicament do not typically exhibit any hydrodynamic properties which would enhance their delivery capability. Furthermore, such compositions cannot provide the dual function of both delivering fluids to and removing them from a chosen site as desired.

One of the dangers of directly inserting a composition into the mouth for the purpose of treating xerostomia is the possibility that the composition will partially degrade or disintegrate during the night or that the user will bite off part of the composition and swallow it. Thus, a serious risk of choking is often presented. On the other hand, when insertion of a device into the mouth is used to treat xerostomia, different kinds of problems are presented: discomfort and damage to tissue areas coming into contact with the device through abrasion or cutting.

What is missing from the prior art is a dual-purpose delivery system for medicaments and moisture including a composition which is viscoelastic and functions as a hydrodynamic pump, easily releasing fluid in a variably controlled manner, and which may be used not only to deliver fluids to a desired site but, if desired, to remove them as well. In addition, such a delivery system must successfully address the issues described above.

SUMMARY OF THE INVENTION

The present invention relates to a hydrogel composition for hydrating and dehydrating dermatological surfaces and to a device for use in conjunction with the composition for delivering moisture and, if desired, medication to a user's mouth in treating xerostomia.

The hydrogel composition is comprised of two polymerizable materials, a polymerization catalyst and a two-part polymerization medium. The polymerizable materials are a hydrophilic acrylate-based monomer and a crosslinking agent. In the preferred embodiment, the polymerizable materials are 2-hydroxyethyl methacrylate and ethylene glycol dimethacrylate, respectively. The polymerization catalyst is a redox initiator system. In the preferred embodiment, a two-part redox catalyst system is used comprised of ammonium persulfate and tetramethyl-ethylene diamine. The polymerization medium is comprised of distilled water and a low molecular weight aliphatic alcohol such as isopropyl alcohol. A hydrodynamic hydrogel composition is formed from a combination of these materials which, after hydration, can release consistent amounts of moisture over a relatively long period of time onto a surface with which it is placed in contact. Alternatively, after dehyration, the composition can absorb moisture from a surface with which it is placed in contact.

A method for forming the hydrogel composition is also provided in which specified percentages by weight of all of the ingredients are mixed to achieve the desired composition. First, the two polymerizable-materials are mixed with the polymerization medium. Then, the ammonium persulfate is added to the preexisting mixture. Only after the ammonium persulfate is thoroughly dissolved may the tetramethyl-ethylene diamine be introduced to the mixture. The resultant composition must be transferred within two to three minutes to a desired mold. The molded composition sets up within between twenty and twenty-five minutes after which it may be removed from the mold and washed to remove the residual monomer from the molded composition.

The device is molded from a thermoplastic material and shaped so as to generally conform to the contours of the interior of a user's mouth. The device is comprised of a center section to each end of which is attached a reservoir section. Each reservoir section has a generally "I" beam shape in which the top and bottom members of the "I" beam generally curve towards each other. A fluid permeable cavity is included in the center support of the "I" beam for receiving and storing medications, fluid and/or flavoring. The center section and each of the reservoir sections include ribbed segments to provide additional flexibility to the device and enable it to further conform to the contours of a user's mouth. In the center section and both of the reservoir sections, small portions of the thermoplastic material are removed to leave holes through the material. When the hydrogel composition is allowed to mold to the device, the holes formed within the thermoplastic material enables the composition to form a strong mechanical bond to the device while the curvature of the top and bottom members helps to more securely retain the composition in contact with the device. The fluid permeable nature of the cavity permits its contents to be delivered and dispersed over time throughout the composition and, hence, onto surfaces with which the composition is placed in contact.

A primary objective of this invention is to provide a hydrogel composition capable of hydrating or dehydrating a surface with which it is placed in contact.

An additional objective of this invention is to provide a hydrogel composition comprised of two polymerizable materials, a polymerization catalyst and a polymerization medium.

It is a further objective of this invention to provide a hydrogel composition based on use of a hydrophilic acrylate-based monomer, a crosslinking agent, a redox catalyst system, a low molecular weight aliphatic alcohol and distilled water.

Yet another objective of this invention is to provide a composition for use as a wound dressing which can either finction to absorb fluids from a wound when used in a dessicated state or to hydrate wounds when applied thereto.

Still a further objective of this invention is to provide a composition for use in implanted hormone or other types of therapy wherein the composition could release medical materials over a prolonged period of time at a controlled rate.

Another objective of this invention is to provide a composition useful in field chemical sampling where it could absorb chemicals in the field and later release in a laboratory.

An additional objective of this invention is to provide a composition for managing dry eyes by hydrating areas around or in contact with the eye.

It is still another objective of this invention to provide a method for making a polymerized hydrogel composition capable of hydrating or dehydrating a surface with which it is placed in contact wherein distilled water, a low molecular weight aliphatic alcohol and two polymerizable materials are mixed together and the first part of a two part redox catalyst system is thoroughly dissolved in the resulting mixture before the second part of the two part redox catalyst system is added to the mixture.

A still further objective of this invention is to provide a composition in which both the moisture release rate and the moisture absorption rate are controllably variable.

Yet an additional objective of this invention is to provide a method for controllably varying the moisture release and the moisture absorption rates of a composition used in hydrating and dehydrating a surface.

It is yet a further objective of this invention to provide a device for use with a composition in treating xerostomia in which the device is molded from a thermoplastic material and is comprised of a center section connected on each end thereof to a reservoir section.

Another objective of this invention is to provide an applicator for treatment of xerostomia comprised of a hydrogel composition and a device onto and through which the hydrogel composition is mechanically bonded wherein the applicator fits comfortably within a user's mouth.

Still another objective of this invention is to provide an applicator for treatment of xerostomia comprised of a hydrogel composition and a device to which the hydrogel composition is bonded wherein the device includes a fluid permeable storage compartment formed therein for delivering medication, fluid and/or flavoring to the composition.

BRIEF DESCRIPTION OF THE DRAWINGS

The foregoing and other objects, aspects and advantages of the invention will be better understood from the following detailed description of the invention with reference to the drawings, in which.

DESCRIPTION OF THE PREFERRED EMBODIMENT OF THE INVENTION

Figure 2:
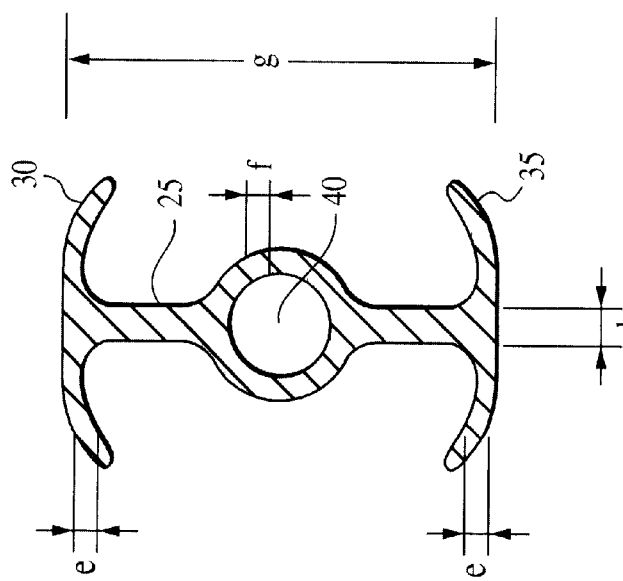
FIG. 2 is a cross-sectional, end view of one reservoir section of the device of the invention.

The integrated delivery system of this invention is comprised of two main components: the composition used to retain medicaments and/or fluids and the mechanical device to which the composition is affixed. Table 1 identifies each element in the composition, the approximate percentage of the whole by weight which that element represents in any given amount of composition prior to initiation of the chemical reaction resulting in formation of the composition. A more detailed description of each element and its affect on the composition follows Table 1.

TABLE 1

| Element | Preferred % by weight | Range % by weight |
| --- | --- | --- |
| HEMA | 26.2 | 26–35 |
| EGDMA | 1.3 | 1–1.8 |
| AP | .4 | 0.3–0.5 |
| TEMED | .2 | 0.1–0.3 |
| Distilled water | 65.4 | 62–72 |
| IPA (reagent grade) | 6.5 | 0–11 |
| Total | 100.0 | |

The composition includes two polymerizable materials. The main polymer is 2-hydroxyethyl methacrylate, or HEMA. It is easily polymerized using thermally activated free radical initiators, i.e. AIBN, or redox catalyst systems. The monomer is water-soluble and the resulting polymer is very hydrophilic but insoluble. If HEMA exceeds approximately 35% by weight of the composition, the water release capability of the composition will suffer. Thus, by increasing the amount of HEMA in the composition, its water release rate would be reduced, while the absorptive rate of the composition would be increased. No substitute monomers are presently known to result in the creation of the same sponge-like hydrogel composition as HEMA when used in the proportions described above. However, several hydrophilic acrylate-based secondary monomers might be substituted for HEMA by adjusting the proportion of other elements in the composition within the ranges presented in Table 1. Such monomers include 2-hydroxy ethylacrylate, 2-hydroxy propylacrylate and 4-hydroxy butylacrylate. The second polymerizable material is ethylene glycol dimethacrylate, or EGDMA, which functions as a crosslinking agent and influences both the rigidity and/or stiffness of the resulting polymer and its release properties. The use of EGDMA results in a crosslinked network that has elastic behavior. The network is insoluble in all organic and aqueous based solvents. The dehydration of the network is reversible if a reusable mechanical device for carrying the composition is provided. EGDMA should represent between approximately 1% and 1.8% of the composition by weight. If less than 1% is used, the composition lacks structural integrity, while if more than 1.8% is used, the composition tends to become chalky and falls apart. Although adjustments from the preferred formulation within the percentage ranges presented in Table 1 would be required to achieve the desired release rate, other crosslinking agents which could be substituted for EGDMA include diethylene glycol dimethacrylate, trimethylpropane triacrylate and trimethylpropane trimethacrylate.

The preferred polymerization initiator is a redox catalyst system which is comprised of ammonium persulfate, or AP, functioning together with tetramethyl-ethylene diamine, or TEMED, to catalyze the polymerization of the HEMA-EGDMA mixture. The use of AP does not influence the properties of the resulting polymer but does directly affect the rate of polymerization. In the preferred embodiment, 0.4% by weight of the AP is dissolved in water along with the other components and once a miscible solution is formed, 0.2% by weight of TEMED is added. The AP reacts with the TEMED to form a free radical on the diamine. This free radical then attacks the unsaturated sites of HEMA and EGDMA. The reaction then propagates from these growth sites. It would also be possible to substitute a thermally activated reaction catalyst such as 2,2'-Azobis(2-methylpropionitrile) for both AP and TEMED. This catalyst becomes thermally activated above 60° C. so that polymerization occurs after heating the mixture of monomer, crosslinking agent, water and isopropanol to this temperature.

The polymerization medium is a combination of water and isopropyl alcohol (IPA). A high concentration of water is required for the heterogeneous porous gel to form. Using water concentrations of less than 62% will result in creation of a homogeneous, clear hydrogel that holds large amounts of water but will not release the water at a desirable rate. Also the use of water allows the composition to be polymerized in a fully hydrated state giving it elastic behavior and permitting residual monomer to be easily removed. The ratio of HEMA to water in the composition affects the appearance, hardness and release rate of the resulting polymer. By increasing the amount of water in the composition, its release rate would be increased, while its absorptive rate would be decreased. However, when the water concentration increases above 72% structural integrity suffers.

The IPA serves three functions. First, by varying the alcohol concentration, both the moisture/medicament release rate and the absorption rate of the hydrogel resulting from the polymerization can be controlled. Increased IPA results in a decreased rate of water release in a mechanically deformed sample of the composition, while also decreasing the rate of water absorption in both a static and mechanically deformed sample of the composition. As a result, a composition having customizable release and absorption rates becomes available. However, when the concentration of IPA exceeds approximately 11% of the composition, the water release rate is reduced so much as to become impractical. By contrast, decreased IPA results in an increased rate of water release in a mechanically deformed sample and in an increased rate of water absorption in either a static or mechanically deformed sample. Moreover, decreased IPA also results in an increase in the maximum amount of moisture which the composition is capable of absorbing. Second, IPA aids in the polymerization of the composition. Gas chromatography results have demonstrated that a composition polymerized with IPA present has substantially less residual monomer remaining at the completion of the reaction than one polymerized without IPA. On average, a typical sample of the hydrogel polymerized with IPA contains residual HEMA of 0.02%, whereas such a sample polymerized without IPA contains residual HEMA of 0.10%. These results indicate use of IPA reduces residual monomer in the polymerized hydrogel by up to 80%. Third, the ability to wash the residual monomer out of the composition is enhanced by the presence of alcohol. This is important since the presence of monomer typically results in a distinctive taste or smell which may appear unpleasant to an eventual user of the composition who would be required to insert it into the oral cavity. If the polymerization medium were 100% water (i.e., representing 72% of the composition by weight and having no IPA), the composition would release an excessive amount of water and would be more malleable than desirable. Various low molecular weight aliphatic alcohols, such as methanol and ethanol, may be substituted for IPA as a secondary diluent without detrimental effect on the resulting composition. However, use of an aromatic alcohol such as benzyl alcohol would result in a polymer lacking structural integrity.

In order to make the composition, the following steps may be followed:

1) Distilled water and IPA (reagent grade) are weighed out in the proportions dictated in Table 1 above. An analytical balance such as the Denver Instruments Model 100 may be used for this purpose.

2) HEMA and EGDMA are weighed out in the same manner.

3) Appropriate amounts of AP are added and allowed to dissolve. The AP must be dissolved before proceeding.

4) After thorough mixing and total dissolution of the AP, the TEMED is added.

The TEMED must be added last. At this point, the worker has approximately 2 minutes to get the water solution in the casting mold or other manufacturing device. After 20 to 25 minutes the polymerization reaction is complete.

5) The composition is removed from the cast media. When shaped test tubes are used as cast media, the device is removed by placing a needle along the edge of the glass at the interface between the test tube and the device. Water is syringed into the bottom of the test tube creating back pressure which forces the appliance out of the mold. Other removal techniques are possible depending on the cast media used.

6) The composition is then soaked in a high concentration environment of water to remove any residual monomer. This washing period lasts for at least 24 hours.

7) The washed composition may then be soaked in an aqueous environment which may be enriched with medicament(s) and/or flavor-enhancers, as desired. It is important to note that adding the reaction mixture to any molding device after evidence of polymerization becomes visible results in an unacceptable composition.

The resultant composition is typically white, opaque and deformable with little force. In addition, it demonstrates a variety of significant features. It remains moist for at least eight hours. Furthermore, it is not chemically altered and does not decompose with dehydration and rehydration. There is no taste or smell associated with the composition as formulated above. It does not support significant growth of microscopic organisms on its surface under conditions analogous to those found in the human mouth. Finally it is both comfortable when applied to human tissue, such as oral tissue, and comfortably conforms to the contours of the anatomical location to which it is applied. Since it is not slippery, it remains in place relatively well once applied to a location. The composition of this invention is a hydrogel but differs from other hydrogels since it is able to both absorb and release fluids. Due to the particular polymerization media used, the composition demonstrates a microporous structure which can be used both to store and disperse fluids and/or medications onto surfaces placed in contact with it and, when not intentionally prehydrated, to absorb fluids from such surfaces. In a dry state, the composition tends to absorb fluids since it is quite hydrophilic, having a high affinity for water. In its hydrated state, due to its inherent hydrodynamic properties, mechanical deformation enables it to drive fluid into or onto an area with which it is in contact.

There are a variety of uses to which the composition may be put including, but not limited to, intervention to prevent fluid loss; wound dressings for absorptive purposes when used in a fully or partially desiccated state at surgical sites, decubitis ulcers, burns and other areas of tissue degradation. Furthermore, the composition can be used for implanted hormone therapy by forming it around a permanent reservoir which may be periodically recharged with medical materials. Still another use for the composition would be for management of abrasions and dry eyes which are a problem very analogous to dry mouth. For example, the loose space beneath the eyes can be implanted with a small wetting device fabricated from the composition, with or without a reservoir, where it functions to relieve dry eye problems. Yet another use of the composition would be inside the human body where it could deliver predefined doses of chemicals or medicaments to be released at controlled rates. By adding a radio-opaque contrast medium such as a barium salt during the manufacturing process, the composition could be located with an x-ray imaging device when used in this manner. Finally, the composition is useful in the area of field chemical sampling since it could absorb liquids in the field and permit transport to the laboratory where liquids could be released for study. The absorptive properties of the composition can be increased by either decreasing the water concentration, decreasing the alcohol concentration or increasing the HEMA concentration. Alternatively, any combination of two or more of these changes in concentrations may be used to achieve the same result.

Figure 1:
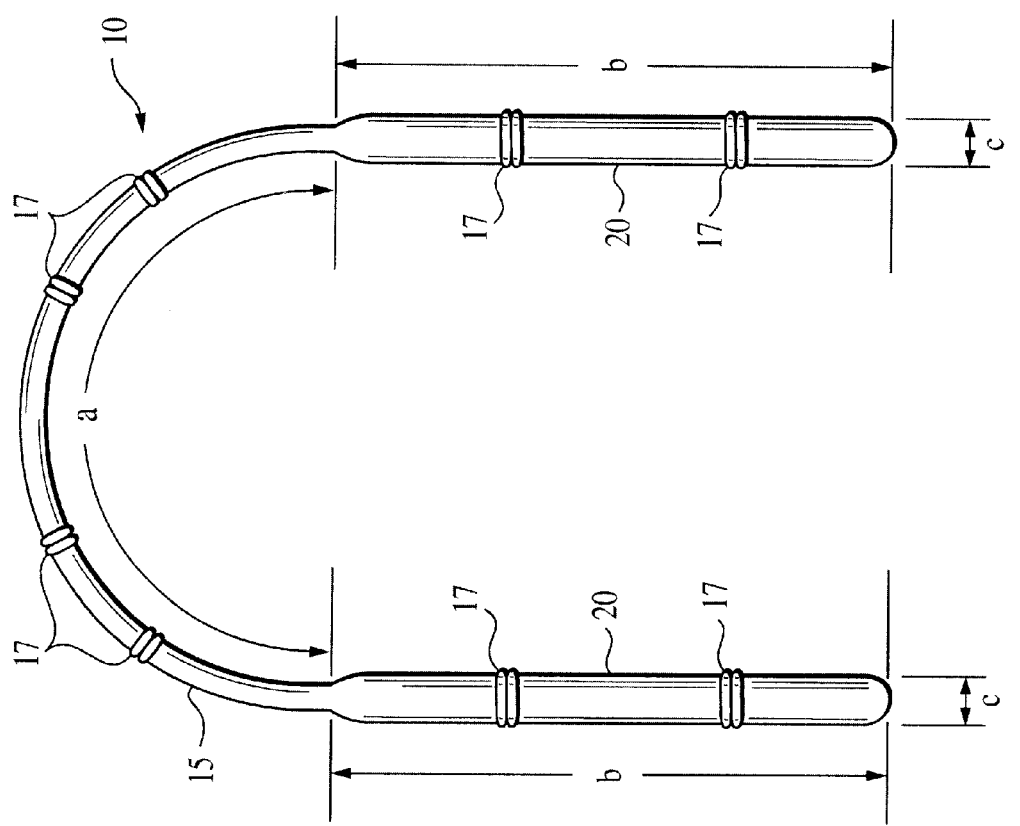
FIG. 1 is an overhead view of the device of the invention.

One important use of the composition is to integrate it with a device which is applied inside the mouths of patients experiencing dry mouth, or xerostomia. For a better understanding of the invention in this context, reference is now made to FIG. 1 of the drawings. This figure shows a top view of device 10 prior to application of the composition to the device. Device 10 is comprised of a center section 15 which is connected on each opposing end to a reservoir section 20.

The device is preferably constructed as a single, molded piece from a thermoplastic material in order to permit it to be molded into the desired intricate shape while retaining its strength, although it may also be molded in two pieces which are subsequently joined together by an adhesive medically acceptable for use in the mouth or by another means suitable for subsequent medical uses. In the preferred embodiment, an amorphous thermoplastic material such as polypropylene or polystyrene is used. An alternative material such as polycarbonate or another moldable thermoplastic could also be used.

Device 10 is molded by a known process into a prebent form conforming to one of several pre-selected anatomically appropriate sizes so as to fit the natural anatomical contours of a wide variety of human buccal and labial vestibules. Similarly, if desired, the device can be custom-formed to the dimensions of a particular user's mouth. By employing such a molding process, the device will have a thermally induced memory which will be retained after cooling into the finally selected form. Additional flexibility is provided in the device by adding bendable ribbed segments 17 to both center section 15 and each reservoir section 20. The ribbed segments are designed to flex only in the lateral direction toward the gums and teeth of the user's mouth. Bendable ribbed segments 17 allow the device to further conform more precisely to various anatomic contours of consumers without having to necessarily make separate custom devices for each user. Each ribbed segment 17 typically comprises two adjacent flexible ribs which extend less than 1 mm beyond the surface of center section 15 and are spaced approximately 3 to 8 mm apart from each other in center section 15 and 10 to 15 mm apart in each reservoir section 20. Thus, in the preferred embodiment of the device there are at least two, and preferably four, such ribbed segments 17 in center section 15 and two such ribbed segments 17 in each reservoir section 20. Other configurations with a larger number of ribbed segments 17 and wherein there are more than two adjacent flexible ribs in each ribbed segment 17 are also possible. The device is preferably molded in a curved shape similar to its final shape in order to minimize the amount of bending stresses to which the device is subjected before it is actually used.

In the preferred embodiment, center section 15 is an elliptically-shaped solid thermoplastic material with its major axis positioned vertically so that it will be parallel to the user's teeth when device 10 is inserted into a user's mouth as described below. This configuration serves both to keep center section 15 as small as possible while preserving material strength and also to maximize user comfort by minimizing the width of foreign material positioned, as described below, in the labial vestibule. The elliptical body may have a length a of up to approximately 3.8 cm, a width along the minor axis of 3 mm or less and a height along the major axis of approximately 10 mm. In the alternative, if minimization of weight of the device is an issue for a particular application, it would be possible to replace solid core center section 15 with a hollow core version but with an increase in the size of the major and minor axes. In still another alternative embodiment, the elliptical shape of center section 15 could be replaced by a reduced-size version of the "I" beam structure of reservoir section 20, discussed next. This alternative structure would further enhance the ability of the composition to adhere to center section 15, although some reduction in user comfort, due to an overall increase in size of center section 15, might result. Each of the reservoir sections 20 typically has a length b of 40 mm or less and a width c of 10 mm or less.

Figure 4:
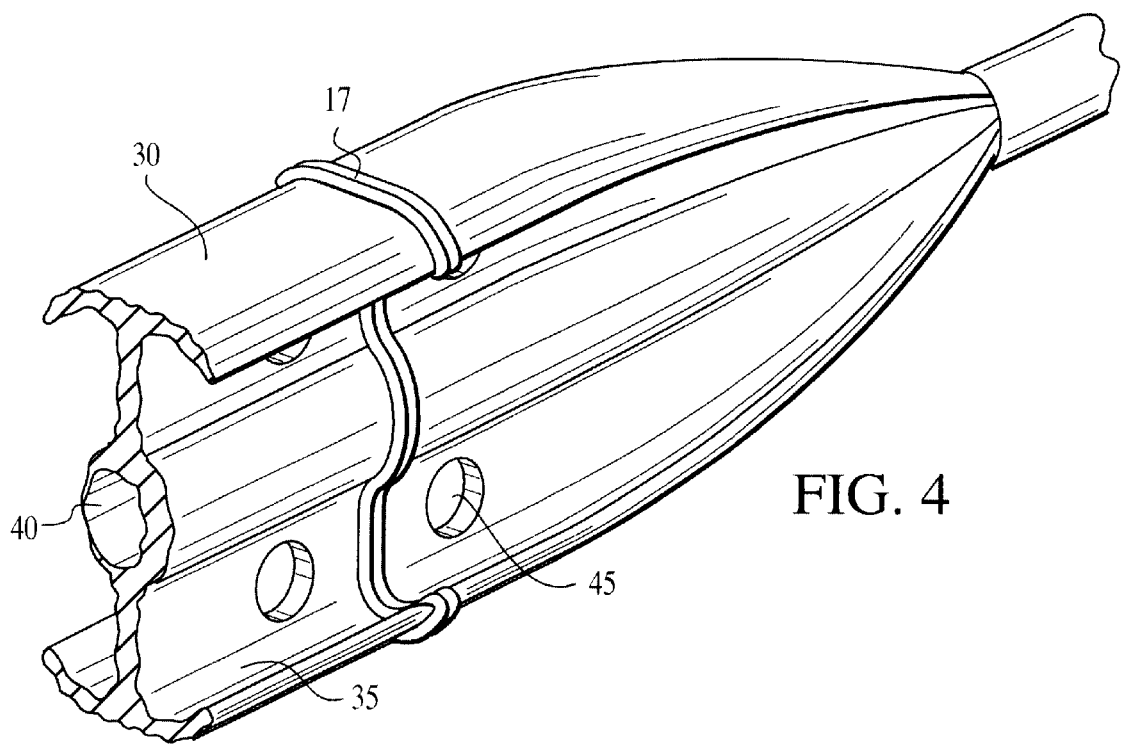
FIG. 4 is a perspective view of the junction of the center section of the device of the invention with a reservoir section.

FIG. 2 shows a cross-sectional view of a reservoir section 20. Like center section 15, each reservoir section 20 is constructed of a thermoplastic material. Each reservoir section 20 resembles an "I" beam, having a center support 25 and top and bottom members, 30 and 35, respectively. Center support 25 has a thickness d of approximately 1.3 mm. The thickness e of the exposed exterior portions of top member 30 and bottom member 35, respectively is approximately 0.65 mm. A cavity 40 may be formed at approximately the middle of center support 25 the walls of which have a thickness f of approximately 0.65 mm. Each cavity 40 extends in a straight line longitudinally within reservoir section 20 from slightly beyond the junction of center section 15 and reservoir section 20, as shown in FIG. 4, to the end of reservoir section 20 displaced furthest away from the junction with enter section 15. Thus, each cavity 40 is enclosed at the end nearest the junction of center section 15 and reservoir section 20, while it is open and exposed at the end of center support 25 terminating at the end of reservoir section 20. Each typical cavity 40 preferably has a volume capacity of approximately 2 cc although this capacity may be altered as required for different medical delivery requirements. Top member 30 and bottom member 35 are each slightly, concavely curved towards each other and have rounded edges along the entire length of each reservoir section 20. The thickness f of the walls forming cavity 40 is approximately 0.65 mm, and these walls are microscopically, fluid permeable. Microscopic porosity may be achieved by numerous means available to those skilled in the art. For example, low molecular weight hydrocarbon wax may be mixed with polypropylene to produce the skeleton structure. By applying solvent to the surface of the skeleton structure after the molding process, wax that was previously distributed on a molecular scale and had been present above the percolation threshold is extracted, thereby assuring continuity of the interior micropores with the exterior micropores. As explained below, each cavity 40 constitutes a storage area into which fluids and/or medicaments may be introduced for eventual dispersal through the permeable walls of cavity 40 into the composition which is ultimately caused to be interlocked with center support 25. For specialized applications, it is also possible to manufacture reservoir section 20 so that there may be multiple cavities 40 formed in either or both reservoir sections 20 or so that only one side of any cavity 40 is fluid permeable, as desired.

Center support 25 has a height g of approximately 1.9 cm as measured from the exterior surface of top member 30 to the exterior surface of bottom member 35. The reason for the curvature and rounded edges in the exterior wall portions of top member 30 and bottom member 35 is to increase the comfort of the device when retained in the mouth of a user by reducing the likelihood of exposure of the gingiva or cheek to sharp edges or blunt surfaces which might be damaging or irritating. The use of curved surfaces on the interior wall portions of top member 30 and bottom member 35 enhances the ability of the composition, once it has been applied to the device and the device has been inserted into the mouth, to make a mechanical bond to the device and to mould to the anatomical contours of the user's jaw and, in addition, provides a gentle, cushioned effect when placed in abutment to a dermatological surface. The dimensions provided for both center section 15 and each reservoir section 20 are only exemplary and may be increased or decreased to accommodate the needs of differently sized devices.

Figure 3:
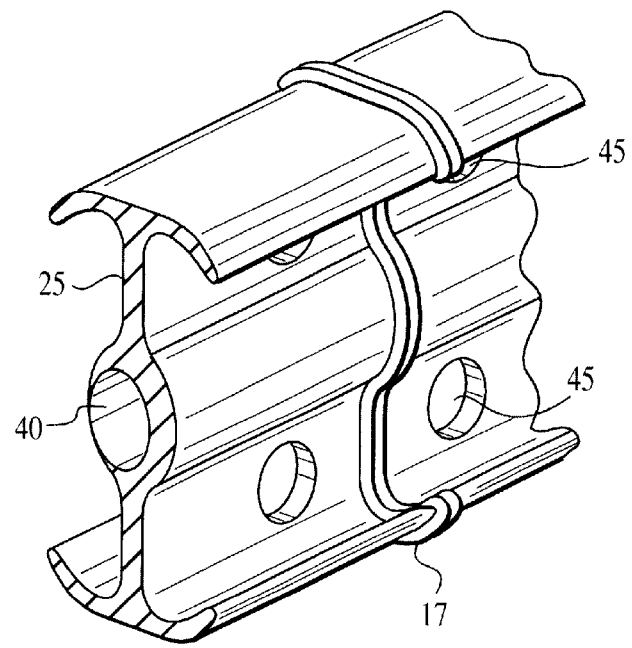
FIG. 3 is a perspective partial view of one end of a reservoir section of the device of the invention.

In FIG. 3, a perspective partial view of a reservoir section 20 including the exposed opening of cavity 40 at one end of reservoir section 20 is shown. Center support 25 includes a plurality of circular holes 45 formed therein from which the thermoplastic material has been entirely removed. In the preferred embodiment there are at least eight such holes having a circular configuration in each reservoir section 20 which may be aligned adjacent to each other and spaced equidistantly approximately 2 mm apart. Four of the holes are situated above cavity 40 and four such holes are situated below cavity 40. Each of the holes 45 has a diameter of approximately 2 mm. By introducing holes 45 into support 25 in an optimized pattern, the overall weight of the device is reduced, material strength is retained and, since the hydrogel composition to be applied to device 10, as described below, is polymerized inside and out, a physical interlock is promoted between the device and the adhesively enhanced composition once that composition is applied to the device, as explained below. In the alternative, multiple, nonaligned holes spaced at different heights in center support 25 could be formed. In such an alternative embodiment, the number of holes in center support 25 may be greater than eight. Although holes 45 are depicted as circular in FIG. 3, other configurations including, but not limit to, triangular, oblong, wavy and irregular may also be used so long as they do not substantially weaken the structural integrity of center support 25 and also enhance the interlock between the device and the composition. Note that in the preferred embodiment, an additional eight holes are formed in center section 15 which are spaced equidistantly approximately 2 mm apart. These holes also function to reduce the weight of device 10 and to promote a stronger mechanical and adhesive bond between the composition and center section 15 by permitting the composition to bond to itself from opposite sides of center support 25. In alternative embodiments, a greater number than eight holes may be formed in center section 15, if desired.

FIG. 4 shows a perspective view of the junction between center section 15 and one of the reservoirs 20. At the junction of each reservoir 20, top member 30 tapers, narrows and curves down toward the junction area, while bottom member 35 tapers, narrows and curves upward towards the junction area.

Figure 5:
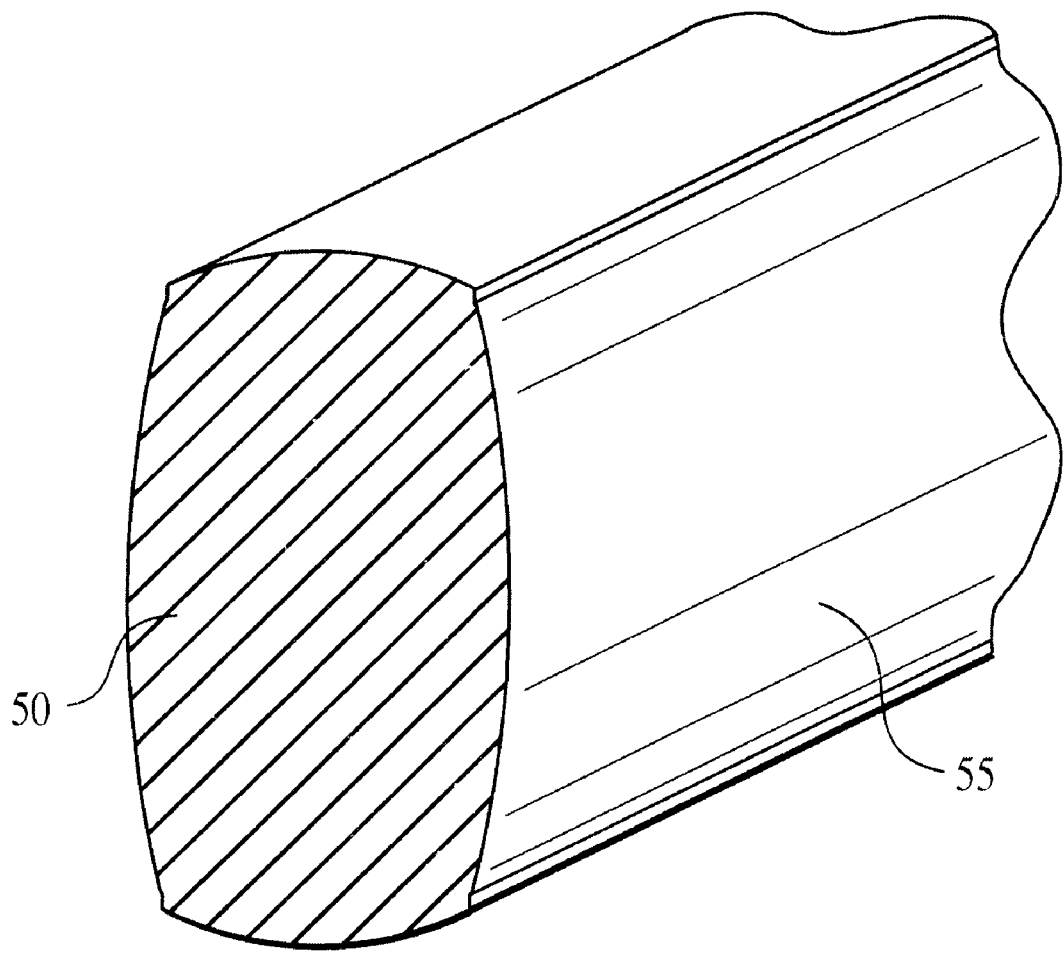
FIG. 5 is a perspective view of one end of one reservoir section of the applicator of the invention.

Once device 10 has been extruded in the desired shape and size and has cooled to room temperature, it is necessary to seal the open end of each reservoir section 20 and apply the composition to the device. The integrated device and composition is hereinafter referred to as the applicator. FIG. 5 shows a perspective view of one end of a reservoir section 20 of the applicator after these steps have been undertaken. In order to seal the open end of each cavity 40 in each reservoir section 20, a single loading portal 50 or separate loading portals for each cavity 40, depending on the configuration of device 10, may be applied. Loading portal 50 may, for example, be a resealable stopper formed from polyethylene, polyurethane or silicone, or any of a variety of other similar elastomeric materials or may be a bladder prefilled with medicament or other fluids. Loading portal 50 may be affixed to the open end of reservoir section 20 in a variety of ways including, through compressive insertion of the stopper into the exposed end of cavity 40 with or without the application of additional adhesive, through application of permanent or removable adhesive along the edges of loading portal 50 where they are designed to contact the walls of cavity 40 or by including a nipple structure on the end of loading portal 50 for insertion into cavity 40 with or without adhesives. The purpose of loading portal 50 is to provide a mechanism for delivery of fluid and/or medicaments into each of the cavities 40 formed within the top and/or bottom members, 30 and 35. Loading portal 50 may include an exterior depression or other marking which corresponds with the location of the cavities 40 so that fluid and/or medicament may be injected by syringe or otherwise into each of the cavities 40. In the event that a bladder is used, the bladder could include discharge areas which are prealigned with the cavities 40. The bladder could be prefilled with medicament and/or fluids prior to sale or delivery to an ultimate user or dispenser. Other methods for delivering medicament and/or fluid into the cavities 40 are also possible.

After the cavities 40 are sealed, an amount of the pre-polymerized composition is mixed and then introduced so as to mold longitudinally along the sides of the reservoir sections 20 and around the center section 15 of device 10. Due to the holes 45 formed in center support 25 of the reservoir sections 20 and in center section 15, the composition flows through and interlocks with device 10. In addition, the composition is further held in close contact with each reservoir section 20 due to the converging concave curving of top member 30 and bottom member 35 on each side of center support 25 of each reservoir section 20. Thus, when produced as described, device 10 is capable of forming a strong mechanical bond with the composition. In addition, the composition is flexible, tear resistant, tasteless and, since it is soft and smooth, is comfortable when in contact with human tissue. Device 10 also remains rigid, retains a memory of its shape and maintains its structural integrity for at least twelve hours when placed in a human mouth as part of the applicator.

A typical application of the composition to the device will require approximately 7.64 grams of composition. Table 2 presents the amount of each element in the composition which is required for such an application.

TABLE 2

| Compound | Grams |
| --- | --- |
| HEMA | 2.0000 |
| EGDMA | .1000 |
| AP | .0300 |
| TEMED | .0125 |
| Distilled water | 5.0000 |
| IPA (reagent grade) | .5000 |
| Total | 7.6425 |

The composition and the device are designed to work together when used in the treatment of xerostomia. Whereas the composition alone is comfortable and will maintain a moist environment for an extended period of time, it is also relatively fragile in that, if used alone, it is subject to being chewed apart by the user when placed inside the mouth. Conversely, the device is not independently comfortable inside the mouth but serves well as a platform to hold and protect the composition while within a user's mouth, thereby providing a long-term environment for release of moisture and medicaments. Through the integrated use of the composition with the device, a balance is achieved between the strength and resilience of the device and the pliant comfort of the composition. In addition, the integrated structure minimizes the likelihood that a user will accidentally bite off, aspirate or swallow pieces of the composition during use of the applicator by substantially protecting the composition from above and below by means of top member 30 and bottom member 35

After the composition has been applied, the applicator is submerged in an aqueous solution to remove unreacted materials and to maintain the applicator in its hydrated state. During exposure to the aqueous solution, the composition remains swollen and assumes a soft, smooth texture. Shaded area 55 in FIG. 5 illustrates the appearance of the composition after it has been applied to a reservoir section 20 of the device. Note that the composition extends horizontally and symmetrically beyond the sides of top member 30 and bottom member 35 in each reservoir section 20 and assumes a generally curved shape. The generally curved shape is controlled by the shape of the mold into which each reservoir section 20 is placed during its encapsulation with the polymerization mixture. Both of these features enhance the fit and comfort of the applicator when placed in the user's mouth since the hydrated composition tends to deform so as to mold itself to the tissue with which it comes into contact.

The hydrated applicator is packaged in a medically appropriate manner such that adequate sterility is maintained, the package is tamper-proof and desiccation or shrinkage of the composition is prevented. Thereafter, the applicator package can be distributed or marketed in any of a number of ways including catalog sales, delivery to pharmacies for over-the-counter sale or to health practitioners for direct use. Shelf life of the applicator is extended since both the composition and the device resist microbiological attack. In order to use the applicator, the consumer or health practitioner removes the device from the package, delivers medicament and/or fluid, as desired and if not previously done, into the cavities 40 through each loading portal 50. Materials may be delivered through loading portal 50, for example, by syringe or by compression, if a bladder type loading portal is used. Thereafter, the applicator is inserted into the mouth in the space between the cheek mucosa and the teeth and gums, known as the buccal vestibule in the molar region and labial vestibule in the incisor region. The device may be used in either the upper or lower jaw. Within 2 to 3 minutes, the hydrogel composition protruding from device 10 molds itself so as to conform to the shape of the user's jaw and gum line. This occurs as a result of the inherent plasticity of the composition and due to the flexibility provided to the applicator by bendable ribbed segments 17. During the wearing period, which can last between eight and twelve hours, the composition releases fluid, flavored or unflavored as desired, together with medicament, if any, into the mouth of the user. Typically, the period of use corresponds with the sleeping period of the user, although that is not a requirement. If desired, additional medicament or fluid may be introduced into the device through the loading portal(s) at the user's discretion. The applicator is typically discarded after use since the composition will develop stress fractures due to dimensional changes that occur during its transition from hydrated to desiccated state. However, in the event that the composition is used independently of the device, once desiccation has occurred, the composition may again be submerged in an aqueous solution, rehydrated, remedicated and reused, although such reuse is limited for hygienic reasons to the same user and typically cannot extend beyond a period of 30 days without unacceptable degradation of the composition.

Another use for the composition either separately or in conjunction with an alternative embodiment of the device is in wound management. It is known that moisture in a noninfected wound promotes healing. Furthermore, clinical studies have shown that dry wound beds actually increase the chance of infection. These principles make use of the composition in wound management ideal. Moreover, the composition, when used in a hydrated state has a nominal binding affinity, meaning that it does not easily adhere to a wound site during periods of application. If the composition is used alone, without the device, it is used much like a bandage. The composition may be packaged in an aqueous solution prior to use in various sizes and shapes. Corresponding to the moist-packaged compositions would be dry-packaged adhesive stripes to hold the composition over the wound. The consumer or health practitioner could position the composition over the wound and then use the adhesive strip or some other type of band to hold it in place. However, if a surface of the composition is exposed to air, it will tend to dehydrate and become brittle or fragile depending on atmospheric conditions and on the location where it is used. Therefore, such wound pads may have a resistant backing with a permeable membrane and a reservoir incorporated therein that will allow medications to be released through the composition while providing some protection from dehydration. It is preferable to provide a mold form to cradle the composition on one side but which, when in use, leave the other side of the composition exposed. If it is preferred to use an applicator, the composition may be cradled in a device analogous to the one used for treating xerostomia but which may be, for example, rectangularly shaped so that it may comfortably mold to the contours of the skin at the wound site and which does not include center section 15 but does include one or more reconfigured reservoir sections 20. Each reservoir section 20 may have a single large or several smaller cavities therein for introduction through one or more appropriately placed loading portals of fluids and or medicaments to encourage uncomplicated healing. This is ideal for septic wounds and burns. An adhesive strip or band holds the device in place. For hygienic reasons, it may be preferable to dispose of an applicator used in this manner after one use although reuse after rehydration is certainly possible. With or without the device, the composition could be packaged with a chemical hot pack or cold pack adhered to it, depending upon the application. This would be especially useful for postoperative and therapeutic applications since it enables temperature control of the wound site as well as possible control of the flow of medication to the wound site.

The foregoing invention has been described in terms of the preferred embodiment. However, it will be apparent to those skilled in the art that various modifications and variations can be made to the disclosed composition and device without departing from the scope or spirit of the invention. The specification and examples are exemplary only, while the true scope of the invention is defined by the following claims.

What is claimed is:

1. A reusable, nonbioadhesive, microporous polymerized hydrogel composition for releasing moisture onto or absorbing moisture from a surface at a variable, controllable and customizable moisture release or moisture absorption rate having two polymerizable materials, a polymerization initiator and a two-part polymerization medium comprised of:
   a first polymerizable material further comprised of a hydrophilic acrylate-based monomer representing between 26% and 35% by weight of composition;
   a second polymerizable material further comprised of a crosslinking agent representing between 1% and 1.8% by weight of the composition;
   a redox catalyst system functioning as a polymerization initiator for said first and said second polymerizable materials comprised of a mixture of between 0.3% and 0.5% by weight of AP and between 0.1% and 0.3% by weight of TEMED;
   distilled water representing between 62% and 72% by weight of the composition; and
   a low molecular weight aliphatic alcohol representing between 0% and 11% by weight of the composition,
   wherein said distilled water and said low molecular weight aliphatic alcohol are the two-part polymerization medium and wherein the moisture release rate of the composition is controllably increased by, prior to formation of the composition, doing any one or more of increasing the percentage by weight of said distilled water used to form the composition within the stated range, decreasing the percentage by weight of said low molecular weight aliphatic alcohol used to form the composition within the stated range while mechanically deforming the composition and decreasing the percentage by weight of said first polymerizable material used to form the composition within the stated range and, further, wherein the moisture absorption rate of the composition is controllably increased by, prior to formation of the composition, doing any one or more of decreasing the percentage by weight of said distilled water used to form the composition within the stated range, decreasing the percentage by weight of said low molecular weight aliphatic alcohol used to form the composition within the stated range and increasing the percentage by weight of said first polymerizable material used to form the composition within the stated range.

2. The composition of claim 1 wherein said first polymerizable material is any one selected from the group consisting of HEMA, 2-hydroxy ethylacrylate, 2-hydroxy propylacrylate or 4-hydroxy butylacrylate.

3. The composition of claim 1 wherein said second polymerizable material is any one selected from the group consisting of EGDMA, diethylene glycol dimethacrylate, trimethylpropane triacrylate or trimethylpropane trimethacrylate.

4. The polymerized composition of claim 1 wherein said low molecular weight aliphatic alcohol is IPA.

5. The composition of claim 1 wherein the maximum amount of moisture which the polymerized composition is capable of absorbing from a surface is increased by decreasing the percentage by weight of said low molecular weight aliphatic alcohol used to form the composition.

6. The composition of claim 1 wherein the composition is elastic and monolithic.

7. A method for controllably increasing the moisture release rate of a reusable, nonbioadhesive, microporous polymerized hydrogel composition having a hydrophilic acrylate-based monomer with a range of between 26% and 35% by weight of the composition, a crosslinking agent with a range of between 1% and 1.8% by weight of the composition, AP with a range of between 0.3% and 0.5% by weight of the composition, TEMED with a range of between 0.1% and 0.3% by weight of the composition, distilled water with a range of between 62% and 72% by weight of the composition, and a low molecular weight aliphatic alcohol with a range of between 0% and 11% by weight of the composition, comprising any one or more of the following steps undertaken prior to formation of the composition:
   increasing the percentage by weight of said distilled water used to form the composition within the stated range;
   decreasing the percentage by weight of said low molecular weight aliphatic alcohol used to form the composition within the stated range and mechanically deforming the composition; and
   decreasing the percentage by weight of said hydrophilic acrylate-based monomer used to form the composition within the stated range.

8. The method of claim 7 wherein the composition is elastic and monolithic.

9. A method for controllably increasing the moisture absorption rate of a reusable, nonbioadhesive, microporous polymerized hydrogel composition having a hydrophilic acrylate-based monomer with a range of between 26% and 35% by weight of the composition, a crosslinking agent with a range of between 1% and 1.8% by weight of the composition, AP with a range of between 0.3% and 0.5% by weight of the composition, TEMED with a range of between 0.1% and 0.3% by weight of the composition, distilled water with a range of between 62% and 72% by weight of the composition, and a low molecular weight aliphatic alcohol with a range of between 0% and 11% by weight of the composition, comprising any one or more of the following steps undertaken prior to formation of the composition:

decreasing the percentage by weight of said distilled water used to form the composition within the stated range;

decreasing the percentage by weight of said low molecular weight aliphatic alcohol used to form the composition within the stated range; and increasing the percentage by weight of said hydrophilic acrylate-based monomer used to form the composition within the stated range.

10. The method of claim 9 wherein the composition is elastic and monolithic.

11. A reusable, nonbioadhesive, microporous polymerized hydrogel composition for hydrating or dehydrating a surface with which the composition is placed in contact at a variable, controllable and customizable moisture release or moisture absorption rate comprised of:

a hydrophilic acrylate-based monomer in the range of 26% to 35% by weight of the composition;

a crosslinking agent in the range of 1% to 1.8% by weight of the composition;

a polymerization initiator;

water in the range of 62% to 72% by weight of the composition; and an aliphatic alcohol in the range between 0% and 11% by weight of the composition.

12. The composition of claim 11 wherein said hydrophilic acrylate-based monomer is any one selected from the group consisting of HEMA, 2-hydroxy ethylacrylate, 2-hydroxy propylacrylate or 4-hydroxy butylacrylate.

13. The composition of claim 11 wherein said crosslinking agent is any one selected from the group consisting of EGDMA, diethylene glycol dimethacrylate, trimethylpropane triacrylate or trimethylpropane trimethacrylate.

14. The composition of claim 11 wherein said polymerization initiator is a redox catalyst system.

15. The composition of claim 14 wherein said redox catalyst system is comprised of AP in the range of 0.3% to 0.5% by weight of the composition and TEMED in the range of 0.1% to 0.3% by weight of the composition.

16. The composition of claim 11 wherein said polymerization initiator is thermally activated.

17. The composition of claim 16 wherein said polymerization initiator is AIBN.

18. The composition of claim 11 wherein said aliphatic alcohol is isopropyl alcohol.

19. The composition of claim 18 wherein use of isopropyl alcohol reduces the amount of residual monomer in the polymerized hydrogel by up to 80%.

20. The composition of claim 11 wherein significant growth of microscopic organisms is not supported.

21. The composition of claim 11 wherein the composition is monolithic and elastic.

22. A method for making a specified amount of a reusable, nonbioadhesive, microporous polymerized hydrogel composition useful for hydrating or dehydrating a surface to which it is applied at a variable, controllable and customizable moisture release or moisture absorption rate and for forming the composition into a desired, molded shape based on use of a two-part polymerization medium, two polymerizable materials and a two-part redox catalyst system for polymerization initiation comprising the steps of:

weighing out an amount of distilled water as the first part of the polymerization medium within the range of 62% and 72% by weight of the amount of composition desired to be made;

weighing out an amount of a low molecular weight aliphatic alcohol as the second part of the polymerization medium within the range of 0% and 11% by weight of the amount of composition desired to be made;

combining the resulting distilled water and the resulting low molecular weight aliphatic alcohol into a mixture;

weighing out an amount of a first, hydrophilic, acrylate-based polymerizable material within the range of 26% and 35% by weight of the amount of composition desired to be made;

weighing out an amount of a second polymerizable material within the range of 1% and 1.8% by weight of the amount of composition desired to be made;

adding the resulting first and second polymerizable materials to the mixture;

weighing out an amount of the first part of the redox catalyst system within the range of 0.3% and 0.5% by weight of the amount of composition desired to be made;

thoroughly dissolving the first part of the redox catalyst system in the mixture;

weighing out an amount of the second part of the redox catalyst system within the range of 0.1% and 0.3% by weight of the amount of composition desired to be made;

adding the resulting second part of the redox catalyst system to the mixture;

transferring the resultant mixture to a mold within approximately two minutes after adding the second part of the redox catalyst system to the mixture;

removing the composition from the mold within between twenty and twenty-five minutes after adding the second part of the redox catalyst system to the mixture; and washing the molded composition in a concentrated water solution for a period of at least twenty-four hours.

23. The method of claim 22 wherein the low molecular weight aliphatic alcohol is IPA.

24. The method of claim 22 wherein the first polymerizable material is any one selected from the group consisting of HEMA, 2-hydroxy ethylacrylate, 2-hydroxy propylacrylate or 4-hydroxy butylacrylate.

25. The method of claim 22 wherein the second polymerizable material is any one selected from the group consisting of EGDMA, diethylene glycol dimethacrylate, trimethylpropane triacrylate or trimethylpropane trimethacrylate.

26. The method of claim 22 wherein the first part of the redox catalyst system is AP which comprises 0.4% by weight of the amount of composition desired to be made.

27. The method of claim 22 wherein the second part of the redox catalyst system is TEMED which comprises 0.2% by weight of the amount of composition desired to be made.

28. The method of claim 22 wherein the composition is elastic and monolithic.

* * * * *